United States Patent [19]

Van der Plank et al.

[11] Patent Number: 5,006,648

[45] Date of Patent: Apr. 9, 1991

[54] PROCESS FOR PREPARING PARTIAL POLYOL FATTY ACID ESTERS

[75] Inventors: Pleun Van der Plank, De Lier; Adrianus Rozendaal, Vlaardingen, both of Netherlands

[73] Assignee: Van den Bergh Foods Co., Division of Conopco Inc., New York, N.Y.

[21] Appl. No.: 76,445

[22] Filed: Jul. 22, 1987

[30] Foreign Application Priority Data

Jul. 23, 1986 [NL] Netherlands .................. 8601904

[51] Int. Cl.$^5$ ............................................. C07H 13/06
[52] U.S. Cl. ................................. 536/119; 536/115; 536/124
[58] Field of Search ................ 536/115, 124, 119

[56] References Cited

U.S. PATENT DOCUMENTS

| | | | |
|---|---|---|---|
| 2,893,990 | 7/1959 | Hass | 260/234 |
| 2,948,717 | 8/1960 | Babayan et al. | 536/119 |
| 3,435,024 | 3/1969 | Nobile et al. | 536/4.1 |
| 3,558,597 | 1/1971 | Van Vrachel et al. | 260/234 |
| 3,600,186 | 8/1971 | Mattson et al. | 99/1 |
| 3,644,333 | 2/1972 | Osipow et al. | 260/234 |
| 3,792,041 | 2/1974 | Yamagishi et al. | 260/234 |
| 3,963,699 | 6/1976 | Rizzi et al. | 260/234 |
| 3,996,206 | 12/1976 | Parker et al. | 536/119 |
| 4,032,702 | 6/1977 | James | 536/119 |
| 4,298,730 | 11/1981 | Galleymore et al. | 536/119 |
| 4,334,061 | 6/1982 | Bossier, III | 536/20 |
| 4,377,685 | 3/1983 | Bouniot et al. | 536/119 |
| 4,496,547 | 1/1985 | Kawashima et al. | 536/115 |
| 4,517,360 | 5/1985 | Volpenhein | 536/119 |
| 4,518,772 | 5/1985 | Volpenhein | 536/119 |
| 4,611,055 | 9/1986 | Yamamoto et al. | 536/115 |
| 4,696,916 | 9/1987 | Yabushita et al. | 514/25 |
| 4,710,567 | 12/1987 | Kea et al. | 536/119 |
| 4,778,881 | 10/1988 | Nieuwenhuis et al. | 536/119 |
| 4,822,875 | 4/1989 | McCoy et al. | 536/119 |
| 4,897,474 | 1/1980 | Bickert | 536/119 |

FOREIGN PATENT DOCUMENTS

| | | |
|---|---|---|
| 50-96518 | 7/1975 | Japan . |
| 51-39621 | 4/1976 | Japan . |
| 1332190 | 6/1978 | United Kingdom . |
| 2081266 | 2/1982 | United Kingdom . |

OTHER PUBLICATIONS

"A Solvent free Synthesis of Sucrose Polyesters", J. Am. Oil Chem. Soc. 55 (1978), 398–401 (G. P. Rizzi and H. M. Taylor).

*Primary Examiner*—Ronald W. Griffin
*Assistant Examiner*—Nancy S. Carson
*Attorney, Agent, or Firm*—Gerard J. McGowan, Jr.

[57] ABSTRACT

A process for preparing partial polyol fatty acid esters, e.g. sucrose or sorbitol esters, is improved by (1) mixing the polyol with an alkaline catalyst such as KOH, NaOH or their carbonates, preferably in aqueous solution or dissolved in $C_{1-5}$ alcohols or ketones at atmospheric pressure and 10°–80° C., (2) preparing a mixture of fatty acid lower alkyl esters with an emulsifier, preferably a fatty acid soap, and (3) adding the alkaline polyol solution to the mixture of (2), whereby preferably the solvent is removed during the addition of (1) to (2), e.g. at 60° C. and 5 mbar.

The reaction is improved so that partial polyol fatty acid esters with at most half of the polyol hydroxy groups being esterified are formed at 110°–145° C. within 1–4 hours.

21 Claims, No Drawings

PROCESS FOR PREPARING PARTIAL POLYOL FATTY ACID ESTERS

The present invention relates to a process for the preparation of partial polyol fatty acid esters, in which one or more fatty acid lower alkyl esters are reacted with a polyol having at least 4 hydroxyl groups in the presence of an alkaline catalyst, and the partial polyol fatty acid esters formed are separated from the other reaction products and starting materials. In particular, this is concerned with a new preparation of partial sucrose esters of fatty acids.

Further, the invention relates to the use of the partial polyol fatty acid esters thus prepared in animal feedstuffs, cosmetics, detergents, foodstuffs and pharmaceutical preparations.

In this specification, what is meant by "partial polyol fatty acid esters" are fatty acid esters of a polyol having at least 4 hydroxyl groups, of which not more than half of the hydroxyl groups have been esterified with fatty acid. For partial sucrose esters of fatty acids this means an average of at most 4 hydroxyl groups esterified with fatty acid.

These compounds are well known emulsifiers suitable for use in food and pharmaceutical products as well as in many other applications.

The most important group of polyols having at least 4 hydroxyl groups as described in literature about this subject is that of the sugar polyols, which group comprises the sugars, namely mono-, di- and tri-saccharides, the corresponding sugar alcohols and derivatives thereof having at least 4 hydroxyl groups. In literature many examples of sugar polyols are described, including the sugars lactose, maltose, raffinose and sucrose, the sugar alcohols erythritol, mannitol, sorbitol and xylitol and the sugar derivative alpha-methylglucoside (=alpha-methylether of glucose). The best known polyol fatty acid esters are the fatty acid esters of sucrose.

The aforementioned process is known. It is described, inter alia, in British patent specification GB No. 1,332,190 (Dai Ichi). For example, sucrose, fatty acid soap and water are mixed such that the sucrose is completely dissolved. To this solution a methyl ester of a fatty acid having 8-22 carbon atoms and a transesterification catalyst are added and the mixture is gradually heated under a gradually decreasing pressure until a substantially completely dehydrated melt is obtained without any substantial loss of fatty acid ester through hydrolysis, after which the resulting melt is kept at a temperature of 110°-175° C. to permit transesterification of the fatty acid methyl ester by the sucrose. Hydroxides, carbonates, bicarbonates, methoxides, ethoxides, and propoxides of potassium, sodium and lithium can be used as the transesterification catalyst.

According to this publication, the presence of soap in the aqueous sucrose solution is required to avoid aggregation of the powdery sucrose. The catalyst has to be added after the mixture of soap and sucrose has been prepared.

A serious disadvantage of this method is foam formation, which can occur during removal of the water, resulting in practical problems during application of this process on a technical scale. Consequently there is still need of a relatively simple process for the preparation of partial polyol fatty acid esters with as little formation of by-products and troublesome foam formation as possible.

It has now been found that partial polyol fatty acid esters, in particular of sucrose, can be prepared in an elegant way if sucrose is first dissolved in aqueous KOH, separately a mixture of methyl esters and soaps is made, after which the alkaline sucrose solution is added to the mixture of soap/methyl ester under vacuum, during which at least part of the water is removed practically instantaneously. If desired, the soaps corresponding to the methyl esters used can be applied. The use of potassium soaps is preferred. After the mixture formed has been dried under vacuum, the mixture is heated to about 110°-140° C. to start formation of the partial sucrose fatty acid esters, which can be seen from the formation of methanol. When the reaction is completed or when either the sucrose or the methyl fatty acid is consumed totally, the formation of methanol will stop, but the reaction can be stopped any time. When the amount of methanol developed is measured, the point at which the reaction must be stopped for a specific degree of conversion can easily be determined.

Based on this finding and further experiments, the invention now provides a process for the preparation of partial polyol fatty acid esters, in which one or more fatty acid lower alkyl esters are reacted with an appropriate amount of a polyol having at least 4 hydroxyl groups in the presence of an alkaline catalyst and the partial polyol fatty acid esters formed are separated from the other reaction products and starting materials, which is characterized in that (1) the polyol is mixed with the alkaline catalyst, forming a liquid system, if required using a non-toxic or easily removable solvent, in which system the alkaline catalyst may react with the polyol forming a catalytically active polyol anion, and (2) this liquid system, optionally after any solvent used has first been removed, is combined with the fatty acid lower alkyl esters preferably containing an emulsifier, and the mixture thus formed is reacted under conditions such that the partial polyol fatty acid esters are formed.

In this specification polyol also comprises a partial fatty acid ester of a polyol having a low degree of substitution, which partial esters are intermediates in the conversion of polyol into polyol fatty acid esters having a higher degree of substitution.

Preferably a sugar polyol is used and particularly sucrose or sorbitol.

Suitable alkaline catalysts include the group consisting of alkali metals and alkaline earth metals, and the alkoxides, bicarbonates, carbonates, hydrides, hydroxides and alloys of these metals. KOH has been found to be particularly suitable as a cheap and effective alkaline catalyst, but also NaOH and the carbonates or bicarbonates of K or Na can be used with advantage. Although it can be argued whether the aforementioned KOH acts as a catalyst or as a reagent, which forms the actual catalyst or catalysts in the process, this description uses the term "catalyst", as does known literature about related reactions.

It is recommendable that in step (1) a solvent be used to improve the contact and, as a result, the reaction between polyol and alkaline catalyst. Suitable solvents include lower alcohols and/or ketones, e.g. a $C_{1-5}$-alcohol or -ketone. For sucrose as polyol and KOH as alkaline catalyst, water is a very suitable solvent.

Step (1) was carried out successfully at atmospheric pressure and room temperature. Partly owing to the solubility of sugar, other temperatures can be used as well, e.g. from 10°-80° C. or even from 40°-70° C. Step (1) can also be carried out at a pressure higher or lower than atmospheric.

For practical purposes the alkaline catalyst of step (1) can be added in a molar ratio of catalyst:polyol of about (0.05-1):1.

In principle many types of alkali-resistant emulsifiers can be used to improve contact of the ingredients in the reaction to be carried out in step (2). Known edible emulsifiers include mono/diglycerides, phosphatides, such as lecithin, and detergents such as soaps, sodium dodecyl sulphate and partial sugar esters of fatty acids.

In a particular embodiment of a process according to the invention, a fatty acid soap is incorporated as emulsifier in the fatty acid lower alkyl esters before the addition of the mixture containing the polyol and alkaline catalyst. The required soap can be made beforehand and be added in dry form. However, it is also quite possible that the fatty acid soap is formed in situ by partial saponification of the fatty acid lower alkyl esters or by neutralization of fatty acids added. In that case it is preferable to use a solvent in which an alkaline substance used for the saponification or neutralization can dissolve to improve the contact and, as a result, the saponification or neutralization. Suitable solvents include lower alcohols, preferably a $C_{1-5}$ alcohol, in particular methanol, and water. Other alkali-resistant solvents can also be used. When a solvent is used, it is recommendable that, after the in situ soap formation, the solvent be removed, e.g. by evaporation, before the resulting mixture containing fatty acid lower alkyl esters and soap is processed further in step (2). The amount of soap is preferably about 2-12 wt. % of the total reaction mixture.

Esters of lower alcohols, preferably of $C_{1-5}$ alcohols, are suitable for use as fatty acid lower alkyl esters. The fatty acids can be $C_{8-22}$ fatty acids, both saturated and unsaturated fatty acids. In the preparation of partial polyol fatty acid esters of $C_{8-12}$ fatty acids, starting from lower alkyl esters of $C_{8-12}$ fatty acids, there is a risk of part of the starting fatty acid lower alkyl esters evaporating; in that case, additional measures are to be taken to collect these starting materials and take them back into the reaction mixture.

It is advisable to use an excess of fatty acid lower alkyl esters and to control the degree of conversion by measuring the amount of lower alcohol developed. The excess of fatty acid lower alkyl esters can be removed during the refining of the reaction product according to known methods, e.g. by using the difference of HL value between the fatty acid lower alkyl esters and the partial polyol fatty acid esters.

In an alternative procedure excess sucrose or other polyol is used, which excess can be removed during the refining because polyols are much more water-soluble than the partial polyol fatty acid esters.

The actual formation of partial polyol fatty acid esters takes place in step (2), which can be carried out at a temperature of about 100°-180° C., preferably 110°-145° C. and at reduced pressure, in particular at about 1-50 mbar.

Although the scope of the invention is not restricted by theoretical statements, on the ground of data known from literature the following reactions can be indicated to illustrate the process according to the invention. It is assumed that in step (1), when sucrose and aqueous KOH are used, a sucrate anion is formed according to the equation $$(sucr.)OH + OH^- === (sucr.)O^- + H_2O,$$

in which "===" means "in equilibrium with".

The relevant equilibrium is established practicallly instantaneously under the conditions used and is largely at the right side. In this connection it could be said that sucrose behaves like a weak acid (cf. J. A. Rendleman, Jr.; Adv. in Carbohydr. Chem. 21 (1966), 209, 239-240, 244 and 246). For all that, when e.g. methyl esters are used, the water present in step (2) should be removed quickly, since the OH-ions still present may cause saponification of methyl esters with the aforesaid equilibrium shifting to the left at the expense of sucrate anion. On prolonged contact of sucrate anion with methyl esters in the presence of water, complete saponification takes place and no sucrate anion is left. When, after removal of the water, the temperature is raised to 110°-145° C., this sucrate anion reacts with a methyl ester molecule according to generally accepted, recent theories on interesterification [cf. J. A. Heldal & P. C. Mork in (Proc.) 11th Scand. Symp. Lipids (1981), 147-152 (Publ. 1982)], in which a fatty acid chain is bound to sugar by means of an ester bond, releasing methoxide anion ($CH_3O^-$). This reacts immediately or simultaneously with a sugar molecule (partially or not partially acylated), with methanol being ultimately formed as visible reaction product.

$$(sucr.)O^- + R-CO-OCH_3 === (sucr.)O-CO-R + CH_3O^-$$

$$CH_3O^- + (sucr.)OH === (sucr.)O^- + CH_3OH$$

This process is continued until all methyl esters have been used or all hydroxyl groups of sucrose have been acylated. Then, no methanol is produced any more and isolation of the partial polyol fatty acid esters can be proceeded to. By measuring the total amount of lower alcohol formed, e.g. methanol, the conversion can be determined, and when the desired degree of conversion is obtained, the reaction can be stopped by cooling.

Separation of the partial polyol fatty acid esters from the other reaction products and starting materials can be brought about by processes known per se, inter alia by using organic solvents, water and/or salting out.

In order to establish the degree of conversion, the amount of methanol released was determined.

Taking sucrose and methyl esters as starting products, after removal of the soap left after the reaction, the reaction product will consist of a mixture of methyl esters and sucrose esters of fatty acids. In a number of cases the hydroxyl number of this reaction product that had been freed of soap was determined, which is also a measure for the degree of conversion, whereby, of course, a correction needs to be made for the content of methyl esters in the reaction product. For example, the theoretical values of the hydroxyl number for sucrose fatty acid esters (SFAE) of groundnut oil fatty acids depends on the degree of conversion as follows:

| SFAE (average number of esterified hydroxyl groups) | Hydroxyl number | Degree of conversion in % |
|---|---|---|
| 8 | 0 | 100.0 |
| 7 | 26 | 87.5 |
| 6 | 58 | 75.0 |
| 5 | 101 | 62.5 |

-continued

| SFAE (average number of esterified hydroxyl groups) | Hydroxyl number | Degree of conversion in % |
|---|---|---|
| 4 | 160 | 50.0 |
| 3 | 247 | 37.5 |
| 2 | 386 | 25.0 |
| 1 | 647 | 12.5 |
| 0 | 1310 | 0.0 |

Another indication of the conversion can be obtained by means of a mass balance for the sucrose esters. In most cases this balance will be in agreement with the conversion of methanol and/or the hydroxyl number found.

The process according to the invention further has, inter alia, the advantage that less foam is formed in the various steps of the process. It has been found that, especially when aqueous KOH is used instead of KOH/methanol, less foam occurs when soap is formed in situ. Likewise, when the water is removed quickly under vacuum, less foam is formed than when KOH/methanol is used.

The foaming problems mentioned do not arise, or to a far lesser degree, when using the process according to the invention, in particular when in step (2) aqueous KOH is used for forming soap in situ from the methyl esters or from the fatty acids and in step (1) for the formation of the liquid system containing polyol and alkaline catalyst.

The invention further relates to the partial polyol fatty acid esters prepared by a process according to the invention.

The invention also relates to a process for the preparation of animal feedstuffs, cosmetic preparations, detergent compositions, foodstuffs or pharmaceutical preparations, in which an effective amount of partial polyol fatty acid ester, which has been prepared according to the invention, is incorporated, e.g. as an emulsifier.

The invention is now illustrated by the following Examples without, however, being restricted thereto.

In Examples I-VIII as emulsifier soap was used which was prepared in situ. In Examples I and VIII this was done by partial saponification, in Examples II-VII by neutralization of fatty acids added. Although the Examples are directed to the preparation of sucrose fatty acid esters having at least 5 hydroxyl groups of the sucrose molecule esterified with fatty acid, it is clear from the degree of conversion given, that partial sucrose fatty acid esters having 1 to 4 hydroxyl groups esterified were present and can be isolated at lower degrees of conversion, e.g. about 12.5%, 25%, 37.5 % and 50% conversion for an average fatty acid content of 1, 2, 3 and 4, respectively, per sucrose molecule.

EXAMPLE I

Step 1

Forming of the liquid system containing the sucrose and alkaline catalyst 25.4 g (74.3 mmol) sucrose and 0.896 g 85% KOH (13.6 mmol) were dissolved in 25 ml water at room temperature and at atmospheric pressure.

Step 2a

Forming of soap 8 g 85% KOH (0.12 mol) dissolved in 60 ml methanol was added to 125 g methyl ester of groundnut oil fatty acids (0.422 mol). The methanol was removed by boiling, followed by drying at 100°-110° C. and 1-2 mbar. Subsequently 225 g (0.760 mol) methyl ester of groundnut oil fatty acids was added.

Step 2b

Reaction

With vigorous stirring at 60° C. and 2 mbar, the sucrose containing alkaline solution of step (1) was added to the reaction product of step (2a), resulting in quick removal of the water during the addition. Thereafter, drying was carried out under the same conditions for about 30 minutes, resulting in a water content of less than 0.04%. Subsequently the temperature was raised to 120° C., after which sugar ester started to form. This could be observed by development of methanol, which was collected in a cold trap.

The molar ratio KOH:sucrose in step (1) was 0.183 and that of methyl ester:sucrose was 14.3. The amount of soap was 10.2%, calculated on the total reaction mixture. The yield of methanol collected after reaction for 10 hours was 88% of the maximum amount of octa-ester calculated theoretically.

EXAMPLE II

As in Example I, sucrose (25.4 g=74.3 mmol) and 85% KOH (1.054 g=16 mmol) were dissolved in water (25 ml). Subsequently a mixture of methyl esters of groundnut oil fatty acids (314 g=1061 mmol) and fatty acids (32.67 g=121 mmol of the product Pristerene 4911$^R$, ex Unichema, mainly consisting of saturated $C_{16-18}$ fatty acids) was prepared, to which a solution of 85% KOH (8 g=121 mmol) in water (10 ml) was added at 60° C. under vacuum. Thereafter, the sucrose/sucrate solution was added to the soap dispersion in about 30 minutes at 60° C. and 2 mbar. Further drying was then carried out for 30 minutes at 60° C. and 2 mbar and the mixture was subsequently heated to 125° C., after which methanol started to develop. After reaction for 10 hours under these conditions, when 95% of the theoretical amount of methanol had been collected, calculated on complete conversion of the sucrose into octa-ester, the reaction was stopped by cooling to about 60° C.

During the 10 hour reaction period the total amount of methanol developed was determined every hour and the average degree of conversion was calculated. The values found were:

| Hours of reaction | 1 | 2 | 3 | 4 | 5 | 6 | 7 | 8 | 9 | 10 |
|---|---|---|---|---|---|---|---|---|---|---|
| % conversion | 6.7 | 12.7 | 22.5 | 45.6 | 71.1 | 81.3 | 86.7 | 90.4 | 92.9 | 95.4 |
| average | 0.5 | 1.0 | 1.8 | 3.6 | 5.7 | 6.5 | 6.9 | 7.2 | 7.4 | 7.6 |

| Partial sucrose fatty acid esters | Sucrose fatty acid polyesters |
|---|---|
| number of fatty acid per sucrose molecule | |

Thus, if the reaction was stopped during the first four hours, the majority of the sucrose fatty acid esters were partial esters, which could have been isolated.

After further processing the reaction mixture according to the BOSSIER method with 2-propanol/water in order to remove the soap, a hydroxyl number of 9.8 was measured.

The molar ratio KOH: sucrose in step (1) was 0.215 and the molar ratio methyl ester:sucrose was 14.3. The weight percentage of soap in the total mixture was 10.2.

EXAMPLE III

Example II was repeated, except that the product Pristerene 4941$^R$, ex Unichema (36.8 g=121 mmol, mainly consisting of saturated $C_{18-22}$ fatty acids) was now used as fatty acid source. The reaction was carried out at 140° C. instead of 125° C. After 6 hours, 99% of the theoretical amount of methanol had been collected. The weight percentage of soap, calculated on the total mixture, was 10.9. The hydroxyl number before steaming but after washing with a mixture of 2-propanol/water for removal of the soap and after drying was 4.

As in Example II, the total amount of methanol developed during the reaction was determined every hour, giving the following values:

| Hours of reaction | 1 | 2 | 3 | 4 | 5 | 6 |
|---|---|---|---|---|---|---|
| % conversion | 12.0 | 56.3 | 84.4 | 93.2 | 96.0 | 99.2 |
| average number of fatty acid per sucrose molecule | 1.0 | 4.5 | 6.8 | 7.5 | 7.7 | 7.9 |
| Partial sucrose fatty acid esters | | | Sucrose fatty acid polyesters | | | |

Thus the partial sucrose fatty acid esters were formed within about 1.75 hours.

EXAMPLE IV

Example II was repeated, except that the product Prifac 7960$^R$, ex Unichema (containing about 60% linoleic acid and about 22% oleic acid) was used as fatty acid source. After reaction for 9 hours, 95% of the theoretical amount of methanol had been collected.

As in Example II, measurement of the total amount of methanol development gave the following conversion:

| Hours of reaction | 1 | 2 | 3 | 4 | 5 | 6 | 7 | 8 | 9 | 10 |
|---|---|---|---|---|---|---|---|---|---|---|
| % conversion | 14.9 | 57.1 | 76.4 | 82.6 | 85.5 | 89.7 | 92.3 | 94.3 | 95.0 | 95.8 |
| average number of fatty acid per sucrose molecule | 1.2 | 4.6 | 6.1 | 6.6 | 6.8 | 7.2 | 7.4 | 7.5 | 7.6 | 7.7 |
| Partial sucrose fatty acid esters | | | | Sucrose fatty acid polyesters | | | | | | |

Thus the partial sucrose fatty acid esters were formed within about 1.75 hours.

EXAMPLE V

Example II was repeated, except that methyl esters of fatty acids of soybean oil were used, hardened to 69° C. (314 g=1061 mmol) and, as fatty acid source, the product Priolene 6930$^R$, ex Unichema (mainly consisting of oleic acid; 33 g=121 mmol). 10 wt. % soap was used, calculated on the total mixture. After reaction for 9 hours, 96% of the theoretical amount of methanol had been collected.

As in Example II, measurement of the total amount of methanol developed gave the following degree of conversion, showing that within about 2.5 hours the partial sucrose fatty acid esters were formed.

| Hours of reaction | 1 | 2 | 3 | 4 | 5 | 6 | 7 | 8 | 9 |
|---|---|---|---|---|---|---|---|---|---|
| % conversion | 10.5 | 25.4 | 61.3 | 80.9 | 87.1 | 90.2 | 92.7 | 95.1 | 96.3 |
| average number of fatty acid per sucrose molecule | 0.8 | 2.0 | 4.9 | 6.5 | 7.0 | 7.2 | 7.4 | 7.6 | 7.7 |
| Partial sucrose fatty acid esters | | | | Sucrose fatty acid polyesters | | | | | |

EXAMPLE VI

Example V was repeated, except that methyl esters of coconut oil fatty acids (244 g=106 mmol) were used and the reaction was carried out at 110°-118° C. 12.5% soap was used, calculated on the total mixture. After 10.5 hours, no methanol was formed any more, after which the reaction mixture was cooled and further processed. If reaction is stopped after about 1-2 hours, mainly partial sucrose fatty acid esters are formed.

EXAMPLE VII

As in Example I, sucrose (254 g=0.743 mol) and 85% KOH (10.54 g=0.16 mol) were dissolved in 250 ml water.

Subsequently a solution of 85% KOH (80 =1.21 mol) in 100 ml water was added to methyl esters of soybean oil fatty acids (3500 g=11.82 mol) at 70° C. under 1 atm. nitrogen. After heating for 1.5 hours at 95° C., water and methanol were removed under vacuum. The sucrose/sucrate solution was then added to the soap dispersion at 60° C. and 2 mbar. After drying under the same conditions, the mixture was heated to 125° C. in order to start the reaction; 12 hours later, 99% of the theoretical amount of methanol had been collected.

The conversion was followed as in Example II, showing that after 1.5 hours the sucrose was converted mainly into partical sucrose fatty acid esters.

| Hours of reaction | 1.5 | 2.5 | 4.5 | 7.5 | 12.0 |
|---|---|---|---|---|---|
| % conversion | 42 | 73 | 86 | 96 | 99 |
| average number of fatty acid per sucrose molecule | 3.4 | 5.8 | 6.9 | 7.7 | 7.9 |

EXAMPLE VIII

A sucrose/sucrate solution was prepared as indicated in Example II. Subsequently 22.0 g of the product Pristerene 4941$^R$, ex Unichema (=72 mmol) was added to methyl esters of groundnut oil fatty acids (314 g=1061 mmol) at room temperature, which mixture was then neutralized by the addition of 85% KOH solution (4.94 g=75 mmol in 6 ml water) at 60° C. under vacuum. Thereafter, the sucrose/sucrate Example II. After drying for 30 minutes under the same conditions, the mixture was heated to 125° C. in order to start the reaction; about 5 hours later, 100% of the theoretical amount of methanol had already been collected.

The time, conversion and average number of fatty acid per sucrose molecule, showing that partial sucrose fatty acid esters were formed during the first 2 hours of reaction, were:

| Minutes of reaction | 105 | 165 | 225 | 285 |
|---|---|---|---|---|
| % conversion | 25 | 68 | 97 | 100 |
| average number of fatty acid per sucrose molecule | 2.0 | 6.2 | 7.8 | 8.0 |

The molar ratio KOH: sucrose in step (1) and methyl ester: sucrose was the same as in Example II. The amount of soap was 6.8 wt. %, calculated on the total mixture.

What is claimed is:

1. A process for the preparation of partial polyol fatty acid esters no more than half of the polyol hydroxyl groups whereof have been esterified with fatty acids by reacting one or more fatty acid alkyl esters with a polyol having at least 4 hydroxyl groups in the presence of an alkaline catalyst, comprising the steps of (a) mixing the polyol with the alkaline catalyst in the presence of a non-toxic and easily removable solvent selected from the group consisting of $C_{1-5}$ alcohols, $C_{1-5}$ ketones and water, at 10° C. to 80° C. to form a liquid system in which the alkaline catalyst may react with the polyol forming a catalytically active polyol anion, (b) combining this liquid system with excess fatty acid lower alkyl ester, (c) after removal of the solvent, reacting the mixture thus formed under conditions such that said polyol fatty acid esters are formed, and (d) separating the partial polyol fatty acid esters so formed from the other reaction products and starting materials.

2. Process according to claim 1, wherein a sugar polyol is used as polyol.

3. The process of claim 2 wherein the sugar polyol is selected from the group consisting of sucrose and sorbitol.

4. Process according to claim 1, wherein the alkaline catalyst is selected from the group consisting of alkali metals and alkaline earth metals, and the alkoxides, carbonates, bicarbonates, hydrides, hydroxides and alloys of these metals.

5. Process according to claim 4, wherein KOH is used as alkaline catalyst.

6. Process according to claim 1, wherein step (a) is carried out at atmospheric pressure.

7. Process according to claim 1, wherein in step (a) the alkaline catalyst is added in an amount such that the molar ratio of catalyst to polyol is in the range of about (0.05-1):1.

8. Process according to claim 1, wherein step (b) is carried out at a temperature of about 100°-180° C., and a reduced pressure.

9. The process of claim 8 wherein step (b) is carried out at a temperature of about 110°-145° C.

10. The process of claim 8 wherein step (b) is carried out at a pressure of 1-50 mbar.

11. The process of claim 1 wherein the fatty acid lower alkyl esters of step (b) include an emulsifier.

12. Process according to claim 11, wherein the emulsifier is a fatty acid soap.

13. Process according to claim 12, wherein the soap is used in an amount of about 2-12 wt. % of the total reaction mixture.

14. Process according to claim 12, wherein the fatty acid soap is formed in situ.

15. Process according to claim 14, wherein the fatty acid soap is formed by partial saponification of the fatty acid esters.

16. Process according to claim 14, wherein the fatty acid soap is formed by neutralization of fatty acids added.

17. Process according to claim 14, wherein in step (b) a solvent is used in which an alkaline substance used for the in situ formation of soap can dissolve.

18. Process according to claim 17, wherein after the in situ soap formation, the solvent used is removed by evaporation before the resulting mixture containing fatty acid lower alkyl esters and soap is further processed in step (b).

19. Process according to claim 17, wherein the solvent is selected from the group consisting of $C_{1-5}$ alcohols and water.

20. Process according to claim 1, wherein the fatty acid lower alkyl esters are selected from the group consisting of esters of $C_{8-22}$ fatty acids and $C_{1-5}$ alcohols.

21. Process according to claim 1 wherein the solvent is water.

* * * * *